United States Patent [19]

Ferrieri et al.

[11] Patent Number: 5,352,679
[45] Date of Patent: Oct. 4, 1994

US005352679A

[54] USE OF RIFAXIMIN AND PHARMACEUTICAL FORMULATIONS CONTAINING IT IN THE TREATMENT OF GASTRIC DYSPEPSIA CAUSED BY HELICOBACTER PYLORI

[75] Inventors: Antonella Ferrieri, Tolé; Leone G. Rotini, Bologna, both of Italy

[73] Assignee: Alfa Wassermann S.p.A., Alanno, Italy

[21] Appl. No.: 83,453

[22] Filed: Jun. 28, 1993

[30] Foreign Application Priority Data

Mar. 23, 1993 [IT] Italy .................. BO93A 000099

[51] Int. Cl.$^5$ ............................................. A61K 31/44
[52] U.S. Cl. ...................................................... 514/279
[58] Field of Search ........................................ 514/279

[56] References Cited

U.S. PATENT DOCUMENTS 4,341,785  7/1982  Marchi et al. .................. 514/279

*Primary Examiner*—Jerome D. Goldberg
*Attorney, Agent, or Firm*—Bucknam and Archer

[57] ABSTRACT

The antibiotic known by the name rifaximin (INN) is active orally in the treatment of gastric dyspepsia caused by bacteria known as *Helicobacter pylori*. Rifaximin may be administered in any oral pharmaceutical form, particularly tablets, capsules, sugar coated tablets, granules and syrups containing from 200 to 2000 mg of active principle, at a daily dosage of between 400 and 2000 mg.

3 Claims, No Drawings

_US 5,352,679_

USE OF RIFAXIMIN AND PHARMACEUTICAL FORMULATIONS CONTAINING IT IN THE TREATMENT OF GASTRIC DYSPEPSIA CAUSED BY HELICOBACTER PYLORI

BACKGROUND OF THE INVENTION

The present invention relates to the treatment of gastric dyspepsia by oral administration of rifaximin.

Two Australian microbiologists, Warren J. R. and Marshall B., reported in Lancet, 1983, 1, 1273–1275, that they had identified in gastric biopsies from patients affected with gastric dyspepsia some curved and storiform bacilli which were initially erroneously believed to belong to the Campylobacter species. Later, Goodwin C. S. et al, Int. J. Syst. Bact. 39, 397–405, 1989, made a more precise classification of the micro-organism, which had no elements in common with the Campylobacter genus, and used the name of Helicobacter pylori, derived from the helical form of the bacterium and from its preferred location in the pylorus. Marshall B. et al., Med. J. Australia, 142, 436–439, 1985 and Morris A., Nicholson G., Am.J. Gastroenterol., 82, 192–199, 1987, demonstrated the pathogenic nature of this bacterium which causes gastritis in man.

McNulty C. A. M. et al., Antimicrob. Agents Chemother., 28, (6), 837–838, 1985 and Shungu D. L. et al., Antimicrob. Agents Chemother., 31, (6) 949–950, 1987, have demonstrated the in vitro activity of several antibiotics against this bacterium. In particular, they demonstrated the vigorous antibacterial in vitro activity of antibiotics containing a beta-bactam group, penicillin, ampicillin, cefoxttin and imipenem, quinolones: norfloxacin and cyprofloxacin, aminoglycosides: gentamicin and erythromycin, and also tetracycline and metronidazole and the lack of in vitro activity of other antibacterial agents like sulfa drugs, trimethoprim, nalidixic acid.

It has been found, however, that the proved antibacterial activity in vitro does not automatically give the antibacterial agents a therapeutic activity in vivo on Helicobacter pylori. Mertens J. C. C. et al, Antimicrob. Agents Chemother., 33, 2, 256–257, 1989, demonstrated that norfloxacin, a powerful quinolone antibiotic, active in vitro against the bacteria with M.I.C. 90% equal to 1 µg/ml, is unable to eradicate Helicobacter pylori in 15 out of 17 patients after a month of treatment.

This therapeutic failure, sharply contrasting with the proved in vitro activity of norfloxacin against Helicobacter pylori, is attributed both to the bacterial resistance, acquired in as many as 9 cases during the antibiotic treatment, and to the fact that the antibiotic does not penetrate sufficiently into the deeper layers of the gastric mucous harbouring the bacteria. The lack of antibacterial action in vivo was further demonstrated by histological data and by the symptoms which remained unaltered.

SUMMARY OF THE INVENTION

An object of the invention is to provide an antibiotic which is active in vivo in patients affected by gastric dyspepsia caused by Helicobacter pylori.

The crux of the present invention resides in the finding that rifaximin (INN), an antibiotic belonging to the rifamycin family, 4-deoxy-4'-methyl-pyrido [1',2',:1,2] imidazo [5,4-c] rifamycin SV, described in the Italian patent 1,154,655 and in the U.S. Pat. No. 4,341,785, demonstrates in vitro antibacterial activity against Helicobacter pylori and is active in vivo in patients affected with gastric dyspepsia caused by Helicobacter pylori. The antibacterial activity of this antibiotic is similar to that of rifampin (Venturini A. P. and Marchi E., Chemioterapia 5, (4), 257–262, 1986), but unlike rifampin has not been absorbed systematically after oral administration (Venturini A. P., Chemotherapy, 29, 1–3, 1983 and Cellai L. et al., Chemioterapia, 3, 6, 373–377, 1984) because of the zwitterion nature of the compound which cannot be absorbed by the gastrointestinal tract (Marchi E. et al., J. Med Chem., 28, 960–963, 1985). Because of these properties, rifaximin has no toxicity at 2000 mg/kg/p.o. in the rat, is unlikely to lead to the formation of resistant strains and also remains active for a long time in the stomach. Because of these properties, the present inventors have investigated the possibility of using rifaximin as a drug to eradicate Helicobacter pylori, a bacterium responsible for many pathologies of the dyspeptic type, difficult to eradicate with normal antibiotics absorbed orally and administered systematically, which also involve serious problems of toxicity and easily provoke resistance.

Rifaximin therefore has first been tested in vitro to gauge the sensitivity of Helicobacter pylori towards the antibiotic and then, after observing its action against this type of bacterium, it has been used in vivo to treat patients with dyspeptic symptoms caused by Helicobacter pylori. The test in vivo confirmed that rifaximin is successful in eradicating Helicobacter pylori completely in one half of the patients treated, an eradication found 30 days after the end of treatment, considerable reduction in the number of bacteria in the remaining one half of patients, a considerable improvement of the dyspeptic syptoms, nausea, vomit, burning, belching, epigastric weight and epigastric pain present before the start of the therapy and total normalization or clear improvement of the conditions of the gastric wall on histological examination.

The object of the present invention is the use of rifaximin (INN) and orally administered pharmaceutical formulations containing it in the treatment of the various forms of gastric dyspepsia such as gastritis, gastroduodenitis, antral gastritis, antral erosions, erosive duodenitis and peptic ulcers, caused by the bacterium known as Helicobacter pylori. All the pharmaceutical forms commonly used for oral administration of a drug may be used within the scope of this invention. In particular, the preferred pharmaceutical forms acting as a vehicle for the present invention are tablets, capsules, sugar coated tablets, granules and syrups containing from 200 to 2000 mg of rifaximin. All these pharmaceutical forms may be prepared according to the methods known by pharmaceutical techniques, with excipients selected among binding agents, dispersing agents, thickeners, lubricants, colouring agents, aromatizers, coatings and bioadhesives suitable for the prescribed pharmaceutical form.

For the tablets, binding agents such as polyvinylpyrrolidone, carboxymethylcellulose, microcrystalline cellulose and gelatin, dispersing agents such as amides, sodium starch glycolate, alginates, reticulated polyvinylpyrrolidone and reticulated sodium carboxymethylcellulose; lubricating agents such as talc, magnesium stearate, stearic acid, silica gel, sodium benzoate and the stearic palmitic ester of glycerol; colouring agents such as iron oxides, titanium dioxide, erythrosin, indigotin; coating agents such as hydroxypropylmethylcellulose, hydroxypropylcellulose and esters of polyacrylic acid; plasticizing agents like polyethylene glycols, acetylated monoglycerides, triacetin and diethylphthalate; bioadhesive agents such as polyacrylic acids, pectins, carboxymethylcellulose, polyvinylalcohols, tragacanth and hydroxypropylmethylcellulose may be used advantageously.

In addition to the binding agents, thickeners, lubricants and bioadhesives described for tablets, granules may also contain sweeteners like sodium saccharin, saccharose, aspartam, xylitol, sorbitol and aroma-adding substances such as aromas of sour cherry, cherry, pineapple, and lemon. Besides the excipients described in the tablets, capsules made of both hard and soft gelatin may also contain surfactants like those known under the name of Tween ®, sodium laurylsarcosinate, saccharose monopalmitate and lipophilic substances such as vegetable oils and oil of vaseline and hydrophilic substances for instance polyethylene glycols in which the gelatin is insoluble.

Lastly, the syrups may contain the same agents described for the granules, with the addition of possible preserving agents, for instance, paraoxybenzoates and surfactants such as those described for the capsules. The therapeutic dose varies according to the body weight and the acuteness of the pathology; a daily dose between 400 and 2000 mg, to be administered in a single dose or divided into 2 or 3 doses, is a suitable therapeutic dose.

The antibacterial activity of rifaximin on *Helicobacter pylori* has been determined in vitro on 8 strains isolated from gastric biopsies using concentrations of the drug between 0.03 µg/ml and 16 µg/ml. The minimum inhibiting concentration (M.I.C.) of rifaximin was found to be between 0.5µg/ml and 2 µg/ml.

The therapeutic efficacy of rifaximin in the treatment of some forms of gastric dyspepsia caused by *Helicobacter pylori* was demonstrated by means of a clinical examination performed on 10 patients showing clear dyspeptic symptoms, nausea, vomit, burning, belching, epigastric weight and epigastric pain and endoscopic diagnoses of gastritis, antral erosion and erosive duodenitis, all caused by *Helicobacter pylori* as shown by the serum examinations to determine the levels of specific class G immunoglobulins against *Helicobacter pylori* using the ELISA technique as described by Vaira D. and Holton J., Gastroenterology, 97, 1069–1070, 1989.

In the form of granules marketed under the brand name NORMIX ®, rifaximin was administered for 14 consecutive days at the dose of 1800 mg per day and after 30 days from the end of treatment various tests were performed which demonstrated the efficiency of the treatment from the various aspects.

The clinical examination showed the almost complete disappearance of nausea, vomit, burning, belching, epigastric weight and epigastric pain, while the endoscopic examination showed the disappearance of gastritis in 7 cases and improvement in 3 cases.

The microbiological examination showed complete eradication of *Helicobacter pylori* in one half of the patients and a sharp reduction of the strains present in the remaining one half, while the histological examination revealed the normalization of the gastric wall in patients in whom the bacterium had been eradicated and a clear improvement of the phlogistic infiltrate with reduction of polymorphonucleates in the remaining patients. Lastly the serum examination showed a 20% reduction in the amount of specific immunoglobulins in those patients in whom the bacterium had been completely eradicated.

The examples described hereinbelow must be taken as a further illustration of the invention but must not be considered as a limitation of the invention itself.

EXAMPLE 1

Sensitivity of *Helicobacter pylori* to Rifaximin 8 strains of *Helicobacter pylori*, isolated from gastric biopsies, were cultivated on a medium of Mueller-Hinton broth (DIFCO 0757-01-4, 9.8 mg/ml of Ca++ ions and 1.1 mg/ml of Mg++ ions) supplemented with 2 g/l of sodium chloride and with 1.35% (W/V) of Bitek agar (DIFCO 0138-01-4). 48 hours after seeding, 3.25% (V/V) of defibrinated horse blood (SCLAVO 87088) or the same quantity of horse serum (FLOW 29-211-54) was added to the medium prepared in plates which were kept at 36° C. for 7 days in a 2.5 l jar in microanaerobic conditions achieved using CampyPak (BBL 71034), activated with controlled de-ionized water, without catalyzer.

10 milligrams of rifaximin were dissolved in sterile conditions in 0.6 ml of 99% methyl alcohol. The solution was diluted with 10 volumes of sterile de-ionized water and aliquots of 0.5 ml were added to 7 ml of medium. Cells of *Helicobacter pylori* collected from the medium and dissolved in Columbia broth (DIFCO 0944-05-4) at a multiplicity of $5 \times 10^4$ CFU/ml were deposited in a volume equal to 10µul on the inoculation areas at the rate of about 50 $CFU/mm^2$ through a calibrated plastic loop. Tests were made of concentrations of rifaximin between 0.03 µg/ml and 16 µg/ml and the evaluation of the minimum inhibiting dose (MIC) gave the following results:

0.5 µg/ml for 1 strain
1 µg/ml for 4 strains
2 µg/ml for 3 strains

EXAMPLE 2

Clinical Examination of Patients Affected with Dyspeptic Symptoms Caused by Gastritis Colonized by *Helicobacter pylori*

At the Institute of Clinical Medicine and Gastroenterology of the Sant'Orsola Hospital of Bologna, 10 patients were selected aged between 45 and 50 years affected with dyspectic symptoms with endoscopic report of gastritis colonized by *Helicobacter pylori*.

Seven of these patients presented diagnosis of gastritis, one of antral erosion and two of erosive duodenitis and all were positive to the Cp-test which indicates the presence of *Helicobacter pylori* with a specificity of 100%.

All patients were treated orally with 1800 mg/day of NORMIX ®, which is the trademark for the composition containing rifaximin. The drug was administered as granules divided into 3 daily doses for 14 consecutive days. Thirty days after the end of the treatment, the 10 patients were subjected to the same tests which had been done before the start of the treatment to monitor the success of the treatment with rifaximin.

Clinical Examination

The symptoms assessed were nausea, vomit, epigastric burning, belching, epigastric weight and epigastric pain. The intensity of the symptoms was expressed according to the following scale:
no sympton=0 slight = 1
fair symptom = 2
serious symptom = 3

The statistical table below was drawn up using the exact probability test of Fisher and the test of Wilcoxon and the results, considered significant when the value of P was <0.05, show a significant and almost complete disappearance of all the symptoms considered.

TABLE 1

| SYMPTOM | PRE-TREATMENT | POST-TREATMENT | STATISTICAL SIGNIFICANCE (*) |
|---|---|---|---|
| NAUSEA | $2.89 \pm 0.21$ | $0.00 \pm 0.00$ | * |
| VOMIT | $1.75 \pm 0.25$ | $0.00 \pm 0.00$ | * |
| EPIGASTRIC BURNING | $2.10 \pm 0.11$ | $0.18 \pm 0.10$ | * |
| BELCHING | $1.80 \pm 0.25$ | $0.28 \pm 0.12$ | * |
| EPIGASTRIC WEIGHT | $1.88 \pm 0.30$ | $0.25 \pm 0.16$ | * |
| EPIGASTRIC PAIN | $1.78 \pm 0.22$ | $0.30 \pm 0.15$ | * |

Endoscopic Examination

The endoscopic examination confirmed the clear clinical improvement, highlighting the disappearance of the gastritis in 7 cases and a considerable reduction of erosive lesions in the remaining 3 cases.

Histological Examination

The histological examination gave an evaluation of the presence and amount of the bacteria and an assessment of the type of gastritis with reference to the density and the localization of the inflannnatory infiltrate; any presence of glandular atrophy, intestinal metaplasia and dysplasia was also highlighted.

Before treatment with rifaximin, the histological examination of the gastric mucous had shown a considerable infiltration of polymorphonucleates in all the patients. Moreover, the bacteria was present in considerable quantities in all the plates examined and in 4 cases glandular atrophy and metaplasia were observed.

Thirty days following the end of treatment with NORMIX ®, complete normalization of the gastric histology was observed in the 5 patients in whom *Helicobacter pylori* had been completely eradicated, while in the remaining 5, in whom a small quantity of *Helicobacter pylori* still remained, there was a considerable improvement of the phlogistic infiltrate with a decrease in the number of polymorphonucleates present in the infiltrate.

Microbiological Examination

The microbiological examinations were done on samples of antral biopsies which were used both for the rapid diagnosis of colonization through the CP-test according to Vaira D. et al., J. Clin. Pathol., 41, 812-813, (1988), and for the cultural isolation of *Helicobacter pylori* in chocolate agar with addition of 2% erythromycin according to Vaira O. et al., Am. J. Gastroenterol., 85, 701-704, (1990).

These tests have confirmed the efficiency of rifaximin therapy, showing complete eradication of *Helicobacter pylori* in 5 patients and the presence of just a few colonies in the remaining 5 patients.

In addition, the test of resistance to rifaximin performed on diagnosis on 20 strains of *Helicobacter pylori* did not show any resistant strain.

Serum Examination

The serum examination was performed using the ELISA technique according to Vaira D. et al., Gastroenterology, 97, 1069-1070, 1989. The serum examination showed a decrease in the rate of specific class G immunoglobulins against *Helicobacter pylori* equal to about 20% in the 5 patients in whom *Helicobacter pylori* was eradicated.

What is claimed is:

1. The method of treatment of a patient affected by gastric dyspepsias caused by *Helicobacter pylori*, which consists of orally administering to said patient a composition in unit dosage form containing rifaximin in the amount of 200-2000 mg per dose.

2. The method according to claim 1 wherein said composition is in the form of a tablet, a capsule, a sugar coated tablet, granules or a syrup.

3. The method according to claim 1 wherein the total daily dose of rifaximin is 400-2000 mgs.

* * * * *